United States Patent
Sommer et al.

(10) Patent No.: US 6,307,096 B1
(45) Date of Patent: Oct. 23, 2001

(54) METHOD FOR MAKING ALIPHATIC DIISOCYANATES

(75) Inventors: Alexa B. Sommer, Pittsburgh; Mary Ann Wittig, Carnegie, both of PA (US); Edwin Ray Hortelano, Charleston, SC (US); Philip E. Yeske, Cologne (DE); Jane F. Ciebien, Charleston, SC (US)

(73) Assignee: Bayer Corporation, Pittsburgh, PA (US)

( * ) Notice: Subject to any disclaimer, the term of this patent is extended or adjusted under 35 U.S.C. 154(b) by 0 days.

(21) Appl. No.: 09/473,097

(22) Filed: Dec. 28, 1999

(51) Int. Cl.$^7$ .................................................. C07C 263/00
(52) U.S. Cl. ............................................................ 560/347
(58) Field of Search ................................................ 560/347

(56) References Cited

U.S. PATENT DOCUMENTS

| | | | |
|---|---|---|---|
| 3,897,314 | 7/1975 | Liebsch et al. | 203/89 |
| 4,864,025 | 9/1989 | Robin et al. | 544/222 |
| 4,871,460 | 10/1989 | Robin et al. | 210/634 |
| 4,871,828 | 10/1989 | Blind et al. | 528/44 |
| 4,918,220 | 4/1990 | Collas et al. | 560/352 |
| 5,962,728 | 10/1999 | Mason et al. | 560/352 |

FOREIGN PATENT DOCUMENTS

97/40081   10/1997   (WO) .

*Primary Examiner*—Robert W. Ramsuet
*Assistant Examiner*—Joseph Murray
(74) *Attorney, Agent, or Firm*—Joseph C. Gil; Thomas W. Roy

(57) ABSTRACT

A method for making an aliphatic diisocyanate by (a) phosgenating an aliphatic diamine in the presence of an inert solvent or gas to form a crude reaction mixture; (b) distilling the crude reaction mixture to form an aliphatic diisocyanate production stream and an aliphatic diisocyanate waste stream; (c) introducing the aliphatic diisocyanate waste stream to a chamber and placing the waste stream under supercritical fluid conditions sufficient to dissolve an appreciable amount of the aliphatic diisocyanate component in the supercritical fluid; (d) separating the dissolved aliphatic diisocyanate component from the waste stream, wherein the remaining waste stream is a supercritically-purged aliphatic diisocyanate waste stream; (e) lowering the pressure sufficiently to precipitate the aliphatic diisocyanate component.

12 Claims, No Drawings

METHOD FOR MAKING ALIPHATIC DIISOCYANATES

FIELD OF THE INVENTION

The invention relates to the field of aliphatic diisocyanate production.

BACKGROUND OF THE INVENTION

Aliphatic diisocyanates are major building blocks for the value-added polyurethane products most commonly used in the coatings industry. There are important differences between aromatic and aliphatic diisocyanate monomers. Aromatic diisocyanates, for instance, are much more reactive than their aliphatic diisocyanate counterparts. Urethane products made from aromatic diisocyanate monomers oxidize more easily than those prepared from aliphatic diisocyanates, especially when exposed to UV-light. The higher resistance to UV light-induced degradation of products prepared from aliphatic diisocyanates make them more useful in high quality exterior coatings where gloss and color retention are most important.

Ongoing demand for aliphatic diisocyanates has increased a long felt need to develop a method for making aliphatic diisocyanates that meets the following criteria. First, the method should be highly selective to aliphatic diisocyanate monomers and dimers (uretdiones) such that only an insignificant amount of the aliphatic diisocyanate is wasted. This would result in a high yield of the aliphatic diisocyanate as well as provide a product stream of high purity. Second, the method should operate at a temperature that is lower than the operating temperatures of distillation processes, so that energy costs can be reduced. This would also help to avoid thermal degradation of the product and undesirable side reactions.

Applicants are not aware of any known method that meets this criteria. Hexamethylene diisocyanate, for instance, is ordinarily produced on an industrial scale by phosgenation of 1,6-hexamethylene diamine in the presence of an inert solvent such as chlorobenzene or ortho-dicloro benzene (see. Ullmans Encyklopädie der technischen Chemi, $4^{th}$ edition (1977), Volume 14, page 350, et. seq.). After phosgenation, the resulting product is generally subjected to vacuum distillation from which two products are separated: (i) a purified hexamethylene diisocyanate (HDI) product and (ii) a "waste stream" (a stream of unpurified oligomeric products). The purified product is collected and the waste stream, (which often contains an appreciable amount of valuable materials, e.g., aliphatic diisocyanate monomers, uretdiones), is disposed of.

The disposal of valuable aliphatic diisocyanate monomers and uretdiones with the waste stream has long been regarded as a significant shortcoming of known aliphatic diisocyanate production methods. Efforts to recover aliphatic diisocyanate monomers and uretdiones from waste streams by subjecting a waste stream to multiple distillation steps have not been successful. This is because multiple distillation techniques increase the amount of high molecular weight oligomers. Purification efforts also require a considerable expenditure of energy and outlay in apparatus. Further, the distillation procedures produce an undistillable residue that is very expensive to dispose of because it contains aliphatic diisocyanate components, i.e., monomers, uretdiones, and isocyanurates.

U.S. Pat. No. 4,918,220 discloses a method for separating and recovering toluene diisocyanate, an aromatic diisocyanate, from residues formed during the production of toluene diisocyanate with supercritical extraction techniques. The patent is directed exclusively to the recovery and separation of toluene diisocyanate from residues. There is no discussion about how aliphatic diisocyanates can be extracted from residues formed during the production of aliphatic diisocyanates. There is no discussion about the intermolecular interactions of aliphatic diisocyanate waste streams in supercritical fluids.

U.S. Pat. No. 4,871,460 discloses the separation and purification of isocyanate condensates, reaction products of isocyanates that are used to make foams. The patent focuses in applying supercritical extraction techniques to crude reaction mixtures and does not discuss how supercritical extraction techniques can be applied to waste streams. The patent does not discuss how supercritical extraction techniques can be applied to selectively extract aliphatic monomers or uretdiones from waste streams. U.S. Pat. No. 4,871,828 is also directed to the separation and purification of isocyanate condensates.

U.S. Pat. No. 4,864,025 discloses substantially pure isocyanurate/polyisocyanates that are produced by extracting impure cyclotrimerized diisocyanates with an inert gas, either in the liquid or supercritical state. The method involves cyclotrimerizing at least one aliphatic, alicyclic or arylaliphatic diisocyanate (in which the isocyanate groups are not directly linked to an aromatic ring) and removing the excess diisocyanate monomer and dimer formed with an inert gas in the liquid state or supercritical state. The patent is directed primarily to applying supercritical extraction techniques for purifying isocyanurates from crude reaction mixtures. The patent, however, does not teach how supercritical extraction techniques can be applied to selectively extract an appreciable amount, e.g., 85% or more of aliphatic diisocyanate monomers or uretdiones from waste streams. The patent does not discuss the conditions that are necessary to selectively extract aliphatic diisocyanate monomers and uretdiones in a commercial-scale method.

It is an object of the invention to develop a method for making an aliphatic diisocyanate that overcomes the disadvantages of known methods.

SUMMARY OF THE INVENTION

The present invention relates to a method for making an aliphatic diisocyanate including the steps of (a) phosgenating an aliphatic diamine in the presence of an inert solvent or a gas to form a mixture containing an aliphatic diisocyanate component; (b) distilling the mixture to form a hexamethylene diisocyanate production stream and an aliphatic diisocyanate waste stream; (c) placing the waste stream under supercritical fluid conditions sufficient to dissolve an aliphatic diisocyanate component in the supercritical fluid; (d) separating the dissolved aliphatic diisocyanate component from the waste stream, wherein the remaining waste stream is a supercritically-purged aliphatic diisocyanate waste stream; (e) lowering the pressure sufficiently to precipitate the aliphatic diisocyanate component. The invention also relates to the supercritically-purged aliphatic diisocyanate waste stream formed by the method. These and other features, aspects, and advantages of the present invention will become better understood with reference to the following description and appended claims.

DETAILED DESCRIPTION OF THE INVENTION

The present invention is based on the discovery that an aliphatic diisocyanate component can be selectively extracted from waste streams with supercritical fluid extraction techniques under certain conditions. The phrase "aliphatic diisocyanate component" refers to an aliphatic diisocyanate monomer, an aliphatic diisocyanate uretdione, or mixtures thereof. Although there may be some aliphatic diisocyanate isocyanurates in the aliphatic diisocyanate component, the aliphatic diisocyanate component does not contain an appreciable amount of isocyanurates because modeling results have suggested that the process is not selective to isocyanurates because of its low solubility in supercritical fluids.

The discovery is remarkable because prior to this invention, supercritical fluid extraction techniques had not been applied to extract aliphatic diisocyanate monomers or uretdiones from waste streams. The level of understanding of intermolecular interactions of aliphatic diisocyanate waste streams in supercritical fluids precluded the possibility of reliably calculating solubility levels in many cases. Further, since it is extremely difficult to conduct experiments under supercritical conditions, namely high pressures and high temperatures, the phase behavior of fluids in this supercritical regime is highly non-ideal. Consequently, thermodynamic modeling techniques capable of predicting the behavior of process mixtures containing aliphatic diisocyanate components could not be developed without substantial experimentation and extensive theoretical and computational work. As such, the supercritical fluid (SCF) regime remained largely unstudied and decaffination of coffee and extraction of essential oils are the only well-known, profitable applications known to date.

The method of the invention involves phosgenating an aliphatic diamine in the presence of an inert solvent or gas to form a crude reaction mixture. The phosgenation is carried out in accordance with techniques known to those in the art using solutions of an aliphatic diamine, i.e., 1,6-hexamethylene diamine, in inert solvents and phosgene solutions in inert solvents. Phosgenation can be carried out in one or more stages, for instance, by formation of suspensions of carbamic acid chlorides at low temperature followed by conversion of the resulting suspensions into polyisocyanate solutions at higher temperatures ("cold/hot phosgenation").

Suitable aliphatic amines include any diamine that has an aliphatically-bound amine group. Examples of such diamines include hexamethylene diamine, isophorone diamine, dicyclohexylmethane 4,4'-diamine. 1,6-hexamethylene diamine is preferred. Suitable inert solvents, both for the aliphatic diamine and for the phosgene, include but are not limited to chlorobenzene or orthodichlorobenzene.

It is critical that the phosgenation occur in the absence of any appreciable amount of aromatic diamines so that aromatic diisocyanates, e.g., toluene diisocyanate, do not form in the reaction mixture. As discussed above, aliphatic diisocyanates are fundamentally different from aromatic isocyanates and the presence of aromatic isocyanates are considered an impurity in this invention. It is also critical that the crude reaction mixture does not contain an appreciable amount of condensates. As discussed above, condensates are used to make foams and are not used to make coatings. Accordingly, the crude reaction mixture and the waste stream generally contain less than 5% preferably less than 3% toluene diisocyanate and/or condensate, based on the weight of the waste stream. Even more preferably, the waste stream does not contain any toluene diisocyanate and/or condensate.

After phosgenation, the crude reaction mixture is distilled and an aliphatic diisocyanate production stream and an aliphatic diisocyanate waste stream form. The waste stream and a solvent are placed in a chamber and subjected to predetermined supercritical conditions sufficient to selectively dissolve the aliphatic isocyanate component in the supercritical fluid. In one version of the invention, this can be done in a continuous method in which a polyisocyanate and a supercritical fluid stream, e.g., a $CO_2$ stream, are brought together in a continuous stream in a static mixer (or any other suitable device) and the mixture is then separated by gravity in a flash chamber.

Supercritical fluids suitable for the method of the invention are known. Under supercritical conditions, a supercritical fluid attains physical characteristics between those of a gas and a liquid. Substantially any gas that has a critical temperature below 120° C. and a critical pressure below 3,000 psi would be a suitable material for use herein. Specific materials that are believed to be suitable for use as supercritical fluids include carbon dioxide, sulfur hexafluoride, xenon, ethane, ethylene fluoroform (Freon 23) and Freon 13. Carbon dioxide is presently preferred.

The pressure at which an appreciable amount of the aliphatic diisocyanate component is soluble is a function of the concentration of the component in the waste stream, the structure of the aliphatic diisocyanate component, and the temperature of the waste stream. The temperature at which the waste stream is subjected is sufficient to enable the aliphatic diisocyanate component to be dissolved in the waste stream. The temperature must be greater than the critical temperature of the solvent. Generally, the operating temperature is about 40° C., and more preferably from about 32 to about 50° C. Such temperatures are substantially lower than the temperatures ordinarily used in distillation techniques.

Generally, to extract aliphatic diisocyanate monomers which do not contain cyclic groups at a temperature of about 40° C., e.g., HDI monomers, from the waste stream, for instance, the waste stream is subjected to a pressure that is generally from about 1100 to about 2260 psi when the concentration of the monomer is from about 0.1 to about 20 wt. %, based on the weight of the waste stream. When the concentration of such monomer is higher, e.g., more than about 20 to about 40 wt. %, based on the weight of the waste stream, the pressure at which the waste stream is subjected is generally from about 1100 to about 2400 psi. When the concentration of the monomer is more than about 40 to about 60 wt. %, based on the weight of the waste stream, the pressure at which the waste stream is subjected is generally from about 1100 to about 1900 psi. When the concentration of the monomer is more than about 60 wt. %, based on the weight of the waste stream, the pressure at which the waste stream is subjected is generally from about 1100 to about 1450 psi.

To extract uretdiones of aliphatic diisocyanate that do not have cyclic groups at a temperature of about 40° C., e.g., HDI uretdiones, from the waste stream, the waste stream is subjected to a pressure that is generally from about 1100 to about 4200 psi when the concentration of the uretdione is from about 0.1 to about 20 wt. %, based on the weight of the waste stream. When the concentration of the uretdiones is higher, e.g., more than about 20 to about 40 wt. %, based on the weight of the waste stream, the pressure at which the waste stream is subjected is generally from about 1100 to about 4860 psi. When the concentration of the uretdiones is more than about 40 to about 60 wt. %, based on the weight of the waste stream, the pressure at which the waste stream is subjected is generally from about 1100 to about 4500 psi. When the concentration of the uretdione is more than about 60 wt. %, based on the weight of the waste stream, the pressure at which the waste stream is subjected is generally from about 1100 to about 3200 psi.

Correspondingly, to extract aliphatic diisocyanate monomers of diisocyanates which contain a cyclic group (but not a cyclically-bound amine group) from the waste stream (cycloaliphatic diisocyanates such as isophorone diisocyanate (IPDI) monomers) at a temperature of about 40° C., the waste stream is subjected to a pressure that is generally from about 1100 to about 3500 psi when the concentration of the monomer is from about 0.1 to about 20 wt. %, based on the weight of the waste stream. When the concentration of such monomer is higher, e.g., more than about 20 to about 40 wt. %, based on the weight of the waste stream, the pressure at which the waste stream is subjected is generally from about 1100 to about 3200 psi. When the concentration of the monomer is from more than about 40 to about 60 wt. %, based on the weight of the waste stream, the pressure at which the waste stream is subjected is generally from about 1100 to about 2900 psi. When the concentration of the cycloaliphatic monomer is more than about 60 wt. %, based on the weight of the waste stream, the pressure at which the waste stream is subjected is generally from about 1100 to about 1450 psi. Suitable pressure ranges for different temperatures and concentrations can be determined utilizing thermodynamic modeling techniques based on the Peng-Robinson equation of state.

The supercritical fluid is introduced into the chamber at a feed rate that is sufficient to accomplish the objects of this invention. After the aliphatic polyisocyanate component has been dissolved, the dissolved aliphatic diisocyanate component is separated from the waste stream by eliminating the undissolved components from the chamber. The soluble components of the system (e.g., HDI monomers, uretdiones, IPDI monomers) dissolve in the supercritical fluid and create a supercritical-fluid rich phase. A small amount of supercritical fluid also dissolves in the remaining waste stream and thereby creates a supercritical fluid-poor phase. The supercritical fluid-poor phase has a higher density than the supercritical fluid-rich phase, thereby enabling the phases to be separated gravimetrically with standard equipment, e.g., a flash drum, centrifuge, and settling vessel. In one embodiment, an extracted aliphatic diisocyanate component (a monomer or uretdione) can be recovered into a different solvent at high pressure to save the cost of recompressing large amounts of gas.

The dissolved aliphatic diisocyanate component is collected and the pressure of the mixture containing the separated dissolved aliphatic diisocyanate is then lowered sufficiently so that the aliphatic diisocyanate component precipitates. The aliphatic polyisocyanate monomers and uretdiones are then collected and reintroduced into the aliphatic diisocyanate production stream. Alternatively, the aliphatic diisocyanate component can be stored for individual use. Uretdiones can be thermally cleaved and the resulting monomers can be reintroduced into the production stream or collected separately. The method is highly selective such that an appreciable amount of aliphatic diisocyanate component dissolves in the waste stream. Generally, the method removes at least about 85% and more preferably at least about 90%, and even more preferably at least about 95% of the aliphatic diisocyanate monomers and uretdiones in the waste stream. It has been discovered that the selectivity for extracting isocyanurates increases when the process is practiced at relatively high pressures, e.g., 300 atm, 400 atm, or more, and higher temperatures, e.g., 100° C. However, practicing the process at these conditions is not preferred.

Although it is not necessary, it can be desirable to use the supercritical fluid in combination with a co-solvent (co-diluent) such as acetone, methanol, propane, and octane. Ordinarily such solvents will be used at levels that are less than about 5 mol %, based on the supercritical fluid solvent stream. The use of such a co-solvent can be extremely useful because it can increase the polarity of the solvent mixture, thereby making the extraction method more efficient (carbon dioxide being weakly polar under supercritical conditions). Also, economic considerations may drive the use of a co-solvent.

The waste stream that remains after the aliphatic diisocyanate component is removed is referred to herein as a "supercritically-purged aliphatic diisocyanate waste stream." Unlike known methods which produce waste streams having an appreciable amount of aliphatic diisocyanate components, the supercritically-purged aliphatic diisocyanate waste stream has a substantially reduced amount of aliphatic diisocyanate components. Generally, the supercritically-purged aliphatic diisocyanate waste stream has less than 0.2 wt. % aliphatic diisocyanate monomers, less than 0.9 wt. % aliphatic diisocyanate uretdiones, based on the weight of the supercritically-purged aliphatic diisocyanate waste stream. As such, the supercritically-purged aliphatic diisocyanate waste stream is also a useful and valuable contribution of the invention.

As such, aliphatic isocyanates produced by the method of the invention are known and include 1,6-hexamethylene diisocyanate, bis (4-Isocyanato-cyclohexyl methane), and isophorone diisocyanate (3-isocyanato-methyl-3,5,5-trimethylcyclohexyl isocyanate). The invention can be practiced in a batch or continuous method, depending on the needs of the particular situation at hand.

The method provides previously unrealized advantages. Since the method is less wasteful than known methods, the method increases the amount of aliphatic diisocyanate produced at a plant. Since the method operates at temperatures that are lower than the operating temperatures of distillation processes, it can reduce the energy costs. The use of the relatively lower temperatures prevents the recovered products from being damaged by heat as in the case of distillation processes. Also, the method can significantly reduce the amount of waste, thereby lowering disposal costs.

The invention is further illustrated but is not intended to be limited by the following examples in which all parts and percentages are by weight unless otherwise specified.

EXAMPLES

Example 1

Initial experiments were performed to evaluate the solubility of HDI monomer and HDI trimer in supercritical $CO_2$. The aim was to selectively extract monomer and trimer from a mixture at unique supercritical conditions.

This analysis was performed on an analytical grade Supercritical Fluid Extractor: Suprex PrepMaster and AccuTrap, available from Suprex, Inc. (no longer in business). The following supplies were used in this investigation: (i) a sample of HDI monomer from Aldrich Chemical Company, (ii) a sample of HDI trimer available from Bayer Corporation as Desmodur N 3300, (iii) Kimwipes manufactured by Kimberly-Clark, (iv) Glass Wool silane treated from Supelco, Inc. It was hoped that supercritical conditions that were most conducive to monomer solubility would be identified as well as those for trimer solubility. The ability to selectively extract each was the goal.

A mixture of HDI monomer and trimer was extracted with supercritical $CO_2$ to determine their solubility in this medium. Kimwipes and glass wool were both rinsed with methylene chloride and dried. They were subsequently extracted with supercritical $CO_2$ using the most stringent conditions that could be accommodated by the available instrumentation (150° C. at 450 atm for 30 min. static flow followed by 30 min. dynamic flow). The apparatus and extraction procedure are detailed below.

A 50/50 sample mixture of HDI monomer and trimer was prepared and used to saturate a previously extracted Kimwipe. Kimwipes provided a solid support for the liquid sample. The isocyanate coated Kimwipe was placed in a 3 ml extractor provided by Suprex. The extractor was then plugged at both ends with extracted glass wool and capped with frit/seals and end cap units. The extractor was placed in the Suprex PrepMaster Unit. Sequential extractions were performed on the extraction vessel at the supercritical conditions listed in the table below. Duplicate extractions were performed at each set of conditions except the last one.

The extracts were collected by the AccuTrap Unit and evaluated by Supercritical Fluid Chromatography (SFC). The AccuTrap was connected to the PrepMaster's system restrictor. The purpose of the restrictor was to provide back pressure to the system and to reduce the exiting supercritical fluid to atmospheric pressure. As the pressure was reduced, the supercritical extraction fluid ($CO_2$) carrying the extracted components dissipated and the components were deposited on the unit's collection column of glass beads. The beads were then flushed with solvent, methylene chloride, which dissolved the deposited extracted components. This solution was then analyzed by SFC to determine its composition. Table 1 shows the settings for the Prepmaster used in the indicated runs.

TABLE 1

PrepMaster Settings

| Run # | Temp. ° C. | Pressure Atm | Type of Flow | Length of Flow | Run # | Density g/ml | Dynamic Volume ml |
|---|---|---|---|---|---|---|---|
| 1 & 2 | 100 | 100 | Static | 30 min. | 1 | 0.191 | 106 |
|  |  |  | Dynamic | 30 min. | 2 | 0.191 | 103 |
| 3 & 4 | 100 | 200 | Static | 30 min. | 3 | 0.488 | 94 |
|  |  |  | Dynamic | 30 min. | 4 | 0.488 | 90+ |
| 5 & 6 | 100 | 300 | Static | 30 min. | 5 | 0.688 | 92 |
|  |  |  | Dynamic | 30 min. | 6 | 0.668 | 96 |
| 7 | 100 | 400 | Static | 30 min. | 7 | 0.760 | 97 |
|  |  |  | Dynamic | 30 min. |  |  |  |

Analysis of the collected extracts showed that the HDI monomer preferentially extracted at 100 atm (Runs 1 & 2) while HDI trimer extracted at 300 atm (Runs 5 & 6).

This approach was repeated to check reproducibility and fine-tune the specific extraction conditions. The results were the same in the repeat experiment. We did determine that only HDI monomer was preferentially extracted at 100 and 150 atm levels with no HDI trimer being removed. Multiple extractions at 300 atm removed the HDI trimer and some higher MW components. However these components were more efficiently extracted at 400 atm.

Example 2

This experiment was performed to determine the components present in the waste stream from the HDI production plant in Baytown that are soluble in supercritical $CO_2$. The aim was to selectively extract monomer, dimer, then trimer from the waste stream at unique supercritical conditions.

This analysis was performed on an analytical grade Supercritical Fluid Extractor: Suprex PrepMaster and AccuTrap. This investigation parallels the one detailed in Example 1. The following supplies were used in this investigation: (i) a sample of waste stream from the HDI production plant, Bayer Corporation, Baytown, (ii) Kimwipes manufactured by Kimberly-Clark, (iii) Glass Wool silane treated from Supelco, Inc.

Initial work started on the supercritical fluid extraction of the waste stream from the HDI production plant in Baytown. This analysis duplicated the procedure used on the previous extraction of a mixture of HDI monomer and trimer, Example 1. We hoped to selectively remove HDI monomer, dimer and trimer from the waste stream. The ability to selectively extract each was the goal. The extracts were collected by the AccuTrap Unit and evaluated by Supercritical Fluid Chromatography (SFC). Instrumental specifics are detailed in Example 1.

A sample of the waste stream from the HDI production plant was prepared according to the procedure detailed in Example 1. Sequential extractions were performed on the extraction vessel at the supercritical conditions listed in the table below. Two consecutive extractions were performed at each set of conditions except the last one. Table 2 shows the settings that were used for the indicated runs.

TABLE 2

PreMaster Settings

| Run # | Temp. ° C. | Pressure Atm | Type of Flow | Length of Flow | Run # | Density g/ml | Dynamic Volume ml |
|---|---|---|---|---|---|---|---|
| 1 & 2 | 100 | 150 | Static | 45 min. | 1 | 0.340 | 230 |
|  |  |  | Dynamic | 60 min. | 2 | 0.340 | 210 |
| 3 & 4 | 100 | 300 | Static | 45 min. | 3 | 0.667 | 185 |
|  |  |  | Dynamic | 60 min. | 4 | 0.667 | 180 |
| 5 | 100 | 400 | Static | 45 min. | 5 | 0.824 | 200 |
|  |  |  | Dynamic | 45 min. |  |  |  |

Analysis of the collected extracts showed that the HDI monomer preferentially extracted at 150 atm (Runs 1 & 2) while HDI dimer extracted at 300 atm (Runs 3 & 4) along with residual monomer and some trimer. The trimer almost exclusively extracted at 400 atm.

Example 3

The invention is practiced on a commercial-scale process. Hexamethylene diisocyanate (HDI) is phosgenated as follows. The first step, carbonation, occurs upon adding gaseous carbon dioxide to a solution of hexamethylene diamine in o-dichlorobenzene. In this step, a carbaminate salt is formed. This slurry is then reacted with a phosgene solution to form the monocarbamoyl chloride. Upon heating, hydrogen chloride is eliminated from the carbamoyl chloride to form the isocyanate. In this acidic environment, the other amine of hexamethyline diamine (HDA) is in equilibrium with the protonated form. The remaining free amine is able to react with phosgene, to form another carbamoyl chloride, which also forms the isocyanate upon heating and elimination of hydrogen chloride. Typically, once the reaction is complete, the reaction mixture is clear. Pure HDI is isolated by removing the solvent and other impurities.

Instead of burning the residue (or HDI waste stream) as is done in ordinary processes, the HDI waste stream is pressurized to approximately 2500 psi, a typical operating pressure for a supercritical extraction process, using either a positive displacement pump, e.g., a reciprocating or rotary pump, or a centrifugal pump. The HDI waste stream is then cooled to approximately 40° C., a typical operating temperature for a supercritical extraction process, using a shell-and-tube heat exchanger with the diisocyanate on the tube side.

In a similar fashion, the solvent stream, typically liquid carbon dioxide, is pressurized to approximately 2500 psi using either a positive displacement pump or a centrifugal pump. The solvent stream is then cooled to approximately 40° C. using a shell-and-tube heat exchanger with the solvent on the tube side.

The HDI waste stream and the solvent stream, both at approximately 40° C. and 2500 psi, are mixed by passing the two streams through a static mixer or a packed tube, or alternatively by using an impinging flow mixer, e.g., a jet mixer. As the HDI waste stream and the solvent stream are mixed, the HDI monomer and uretdione present in the waste stream dissolve preferentially in the solvent forming a solvent-rich phase. At the same time, a small quantity of the solvent, typically carbon dioxide, dissolves in the now supercritically purged HDI waste stream forming a solvent-poor phase.

The density of the solvent-rich phase is less than the density of the solvent-poor phase; therefore, the two phases are separated in either a flash chamber, or by some other gravimetric method, e.g., centrifugation. Typically a flash chamber is used, and the solvent-rich phase is collected from the upper part of the chamber at approximately 40° C. and 2500 psi, whereas the solvent-poor phase flows out of the lower part of the chamber at roughly the same temperature and pressure.

A second flash chamber is used to step-down the pressure and temperature of the solvent-rich phase in order to recover a portion of the solvent at a pressure significantly higher than atmospheric pressure, thereby reducing the energy required to recompress the solvent up to the extraction pressure. A shell-and-tube heat exchanger may be used to cool the solvent-rich phase before it enters the second flash chamber. Both the solvent recycle stream and the concentrated solvent-rich stream leave the second flash chamber at approximately 30° C. and 725 psi.

In a third flash chamber, the extracted HDI monomer and uretdione are separated from the remaining solvent in this solvent-rich stream. The HDI monomer and uretdione are recovered at approximately 30° C. and ambient pressure. The remaining solvent is either vented (as in the case of carbon dioxide), or collected for disposal.

Concurrent with the separation processes described above, the solvent-poor phase from the first flash chamber is purged of solvent in a fourth flash chamber. The supercritically purged HDI waste stream is collected from the lower portion of the flash chamber, while the remaining solvent is vented or collected from the upper portion of the flash chamber.

Although the invention has been described in detail in the foregoing for the purpose of illustration, it is to be understood that such detail is for that purpose and that variations can be made therein by those skilled in the art without departing from the spirit and scope of the invention.

What is claimed is:

1. A method for making an aliphatic diisocyanate comprising the steps of:

(a) phosgenating an aliphatic diamine in the presence of an inert solvent or gas to form a crude reaction mixture;

(b) distilling the crude reaction mixture to form an aliphatic diisocyanate production stream and an aliphatic diisocyanate waste stream;

(c) introducing the aliphatic diisocyanate waste stream to a chamber and placing the waste stream under supercritical fluid conditions sufficient to dissolve an appreciable amount of the aliphatic diisocyanate component in the supercritical fluid;

(d) separating the dissolved aliphatic diisocyanate component from the waste stream, wherein the remaining waste stream is a supercritically-purged aliphatic diisocyanate waste stream;

(e) lowering the pressure sufficiently to precipitate the aliphatic diisocyanate component.

2. The method of claim 1, wherein the precipitated aliphatic diisocyanate component is reintroduced into the aliphatic diisocyanate production stream.

3. The method of claim 1, wherein the precipitated aliphatic diisocyanate component is stored for individual use.

4. The method of claim 1, wherein the waste stream comprises a monomeric aliphatic diisocyanate without a cyclic group.

5. The process of claim 4, wherein the monomeric aliphatic diisocyanate is extracted at a temperature ranging from about 32 to 50° C.

6. The process of claim 5, wherein (a) if the concentration of the monomer is from about 0.1 to about 20 wt. %, based on the weight of the waste stream, the waste stream is subjected to a pressure that is from about 1100 to about 2260 psi;

(b) if the concentration of such monomer is from about 20 to about 40 wt. %, based on the weight of the waste stream, the pressure at which the waste stream is subjected is generally from about 1100 to about 2400 psi;

(c) if the concentration of the monomer is from about 40 to about 60 wt. %, based on the weight of the waste stream, the pressure at which the waste stream is subjected is generally from about 1100 to about 1900 psi; and (d) if the concentration of the monomer is more than about 60 wt. %, based on the weight of the waste stream, the pressure at which the waste stream is subjected is generally from about 1100 to about 1450 psi.

7. The method of claim 1, wherein the waste stream comprises a monomeric aliphatic diisocyanate with a cyclic group.

8. The method of claim 1, wherein (a) if the concentration of the monomer is from about 0.1 to about 20 wt. %, based on the weight of the waste stream, the waste stream is subjected to a pressure that is generally from about 1100 to about 3500 psi;

(b) if the concentration of such monomer is from about 20 to about 40 wt. %, based on the weight of the waste stream, the pressure at which the waste stream is subjected is generally from about 1100 to about 3200 psi;

(c) if the concentration of the monomer is from more than about 40 to about 60 wt. %, based on the weight of the waste stream, the pressure at which the waste stream is subjected is generally from about 1100 to about 2900 psi; and (d) if the concentration of the cycloaliphatic monomer is more than about 60 wt. %, based on the weight of the waste stream, the pressure at which the waste stream is subjected is generally from about 1100 to about 1450 psi.

9. The method of claim 1, wherein the waste stream comprises an aliphatic diisocyanate uretdione without a cyclic group.

10. The process of claim 9, wherein the monomeric aliphatic diisocyanate is extracted at a temperature of about 40° C., wherein (a) if the concentration of the uretdione is from about 0.1 to about 20 wt. %, based on the weight of the waste stream, the waste stream is subjected to a pressure that is from about 1100 to about 4200 psi;

(b) if the concentration of the uretdiones is from about 20 to about 40 wt. %, based on the weight of the waste stream, the pressure at which the waste stream is subjected is generally from about 1100 to about 4860 psi;

(c) if the concentration of the uretdiones is from about 40 to about 60 wt. %, based on the weight of the waste stream, the pressure at which the waste stream is subjected is generally from about 1100 to about 4500 psi; and (d) if the concentration of the uretdione is more than about 60 wt. %, based on the weight of the waste stream, the pressure at which the waste stream is subjected is generally from about 1100 to about 3200 psi.

11. The method of claim 1, wherein the waste stream comprises a monomeric aliphatic diisocyanate uretdione with a cyclic group.

12. The method of claim 1, wherein the aliphatic diamine is phosgenated in the absence of any appreciable amount of a component comprising a member selected from the group consisting of aromatic diamines and condensates.

* * * * *